(12) United States Patent
Byrne

(10) Patent No.: US 6,485,412 B1
(45) Date of Patent: Nov. 26, 2002

(54) ADAPTER FOR THE CONNECTION OF A WATER BOTTLE TO AN ENDOSCOPE

(76) Inventor: Donny M. Byrne, 9 Royal Dalton, Conroe, TX (US) 77304

( * ) Notice: Subject to any disclaimer, the term of this patent is extended or adjusted under 35 U.S.C. 154(b) by 120 days.

(21) Appl. No.: 09/880,150

(22) Filed: Nov. 6, 2000

Related U.S. Application Data

(63) Continuation-in-part of application No. 09/166,731, filed on Oct. 5, 1998, now Pat. No. 6,210,322.

(51) Int. Cl.[7] ............................................... A61B 1/015
(52) U.S. Cl. ....................................................... 600/158
(58) Field of Search ................................ 604/257, 403, 604/405, 19, 27, 533; 600/156, 158, 159; 222/189.09, 189.06

(56) References Cited

U.S. PATENT DOCUMENTS

| | | | | | |
|---|---|---|---|---|---|
| 4,301,799 A | * | 11/1981 | Pope et al. | ............... | 222/189.1 |
| 4,552,130 A | * | 11/1985 | Kinoshita | ................... | 600/158 |
| 4,667,655 A | * | 5/1987 | Ogiu et al. | ................. | 600/132 |
| 4,760,838 A | * | 8/1988 | Fukuda | ....................... | 600/158 |
| 5,133,336 A | * | 7/1992 | Savitt et al. | ................ | 600/103 |
| 5,195,664 A | * | 3/1993 | Rhea | ........................... | 222/382 |
| 5,297,537 A | * | 3/1994 | Savitt et al. | ................ | 600/109 |
| 5,437,654 A | * | 8/1995 | McVay | .................. | 222/189.06 |
| 5,611,459 A | * | 3/1997 | Hinch | ........................ | 277/591 |
| 5,707,351 A | * | 1/1998 | Dorsey, III | .................. | 604/30 |
| 5,807,313 A | * | 9/1998 | Delk et al. | ................... | 604/151 |
| 5,830,128 A | * | 11/1998 | Tanaka | ....................... | 137/433 |

* cited by examiner

Primary Examiner—John P. Leubecker
(74) Attorney, Agent, or Firm—Harrison & Egbert

(57) ABSTRACT

An adapter for a disposable water bottle for an endoscope having a cap with threads suitable for attachment to threads on a neck of the water bottle, an outer tube affixed to an opening in the cap, an inner tube extending through the outer tube so as to form an air passing annulus on the interior of the outer tube, and a fitting affixed to an end of the inner and outer tubes opposite the cap. The fitting is adapted for attachment to the air and water connections of the endoscope. A first gasket member is affixed to an interior surface of the cap and a second gasket member is affixed to the first gasket member such that the first gasket member is sandwiched between the second gasket member and the interior surface. An annular member is secured within a hole formed in the fitting and has a slot receiving a protrusion formed in the hole of the fitting.

20 Claims, 8 Drawing Sheets

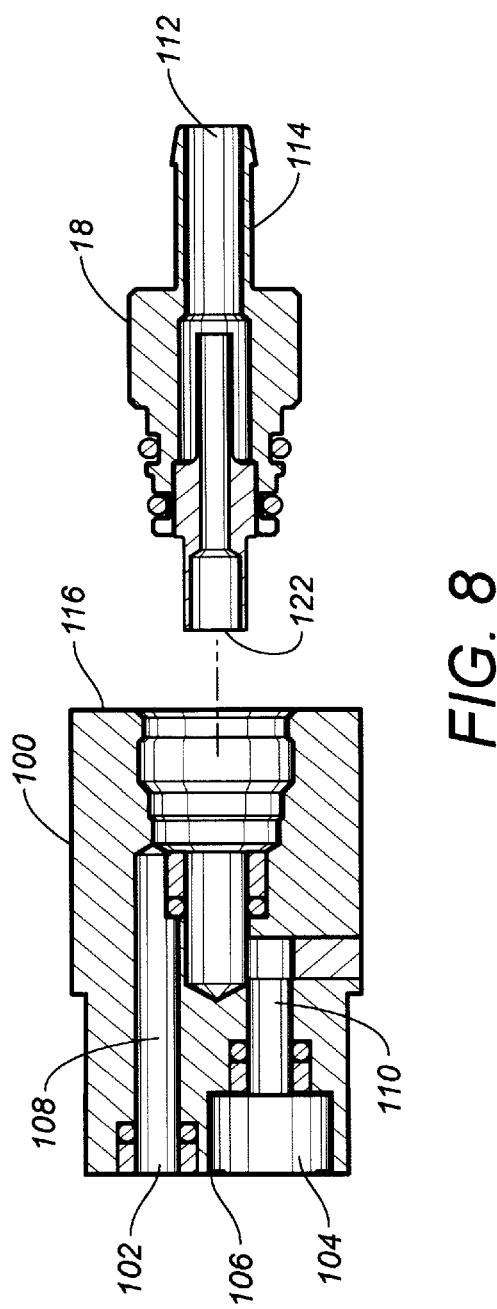
FIG. 8
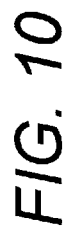
FIG. 10
FIG. 9
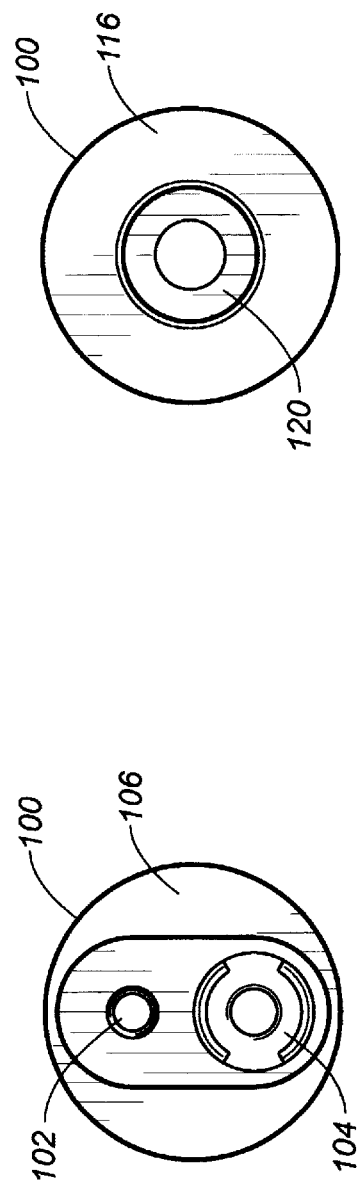

ADAPTER FOR THE CONNECTION OF A WATER BOTTLE TO AN ENDOSCOPE

RELATED APPLICATION

The present application is a continuation-in-part of U.S. patent application Ser. No. 09/166,731, filed on Oct. 5, 1998, and entitled "ADAPTER FOR THE CONNECTION OF A WATER BOTTLE TO AN ENDOSCOPE", now U.S. Pat. No. 6,210,322.

TECHNICAL FIELD

The present invention relates to endoscopic systems. More particularly, the present invention relates to water bottles as used with endoscopic systems. Furthermore, the present invention relates to delivery tubes for passing the water from a water bottle to the optical head of the endoscopic instrument.

BACKGROUND ART

Endoscopic instruments have been developed to provide surgeons with an internal view of the organ or body passage requiring treatment. Such endoscopes typically have channels through which a miniaturized forceps, commonly called flexible instruments, are inserted and advanced. The endoscope assembly includes an elongated flexible cable equipped at one end with an eyepiece or other viewing means and at the other end with an optical head. Only the head is directly and externally connected to the instrument. The cable transmits images or image-producing signals from the illuminated operative site to the viewing means so that the surgeon will have visual confirmation of the action of the instrument's working end. A coherent optic bundle extends from the head and through the flexible cable through the eyepiece for providing the surgeon with visual confirmation of the instrument's tip or jaw action. The illuminating means may take the form a light-transmitting waveguide extending through the cable to illuminate the operative area. The waveguide is connected at its proximal end to a suitable high-intensity light source. The cable also provides a flow passage for the delivery of fluid (liquid or gas) for irrigation or other purposes. Typically, the flow passage and the illuminating means are disposed on opposite sides of the coherent image-transmitting waveguide. In conventional practice, it is necessary to provide the optic head with a flow of sterile water. The passage of the sterile water across the optic head prevents the buildup of materials on the optic head. This flow of water operates, in a sense, like a windshield wiper/washer assembly.

In normal practice, the endoscopic instrument has a control body which is connected by a light guide tube to a light guide connector. The connector will include a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic head of the instrument.

Unfortunately, there is usually a great expense associated with the delivery of such sterile water to the control body. In past practice, the sterile water has been provided from a water bottle that is directly connected to a tube. The tube will have a fitting at one end so as to allow the tube to be connected to the air/water inlet of the light guide connector or to the auxiliary water port on the control body. Typically, the fitting will include an inner tube and an outer tube. The outer tube extends into the water bottle. The outer tube is connected to the cap of the water bottle. In normal practice, air is delivered through the area between the inner tube and the outer tube so as to pressurize the interior of the water container. This will force water to flow through the tube and into the endoscope at a desired rate.

After usage, the water bottle, the tubing, and the associated fittings are sterilized. This creates a considerable wasteful expense to the hospital. If the water is sterilized, there is a considerable labor expense associated with the autoclaving of the bottle. There is also the possibility of residual contaminants residing in the area of connection between the tubes and the bottle.

In the normal hospital environment, sterile water is conventionally provided in one liter bottles. Virtually all of the bottles have the same size of threaded opening. These water bottles are very different, in configuration, from the water containers associated with the prior art water delivery systems for the endoscopic instrument. Typically, existing one liter water bottles in hospitals will be sealed closed by threadedly connecting the interior threads of a cap over the exterior threads on the neck of the bottle.

A new system of endoscopes has been provided which has an unusual adapter for connecting the water bottle to the endoscope. The new 140 series of endoscopes has a pair of female fittings on the adapter for the delivery of air and water to the male fittings of the endoscope. FIGS. 5–7 show this existing prior art system of connection to the 140 series endoscopes.

In FIG. 5, it can be seen that there is a specialized water bottle 60 which has a lid 62 having a tube connection 64 thereon. The tube connection 64 connects to tube 66 which extends to the metal tip 68. A cleaning cap is provided on the metal tip 68. The tube 66 and the tip 68 serve to deliver sterile water from the container 60 to the endoscope.

FIG. 6 shows the 140 series endoscope 72 having a water supply connector 74 and an air connector 76. The water supply connector 74 is a male connector. The air connector 76 is also a male connector. Connector 74 serves to pass water from the water bottle to the interior of endoscope 72, connector 76 serves to pass air from the endoscope to the water bottle.

FIG. 7 shows an end view of the metal tip 68. As can be seen, the metal tip 68 has a female water connector 78 and a female air connector 80. The female water connector 78 is suitable for connection to the male water connector 74 on the endoscope 72. The female air connector 80 is suitable for connection to the male air connector 76 on the endoscope 72.

The new configuration of water container system as shown in FIGS. 5–7 serves to make obsolete the existing expensive water containers and associated tubing and adapters which are used for other endoscopes. As such, as hospitals purchase the new 140 series endoscope 72, they are required to also purchase the new water container 60, the new tubing 66, and the new metal tip 68. The water containers that have been used for prior endoscope systems must also be supplied for any prior endoscope systems that the hospital may have in use. As a result, hospitals are required to manage and maintain inventory of water bottles such as those shown in FIGS. 5–7 and also water containers for their existing endoscope systems. As such, a need has developed so as to allow for the standardization of the water containers for the various endoscope systems which are offered. Any standardization that can be achieved will eliminate the need to maintain inventory for each of the various types of endoscopes which a hospital employs.

Presently, the disposable water bottles are manufactured in 250 milliliter, 500 milliliter and 1,000 milliliter sizes. These water bottles have slightly varying diameter necks of slightly varying lengths. The thread structure on the neck of each of these water bottles is slightly different. The difference in length of neck and configuration of threads is the result of water bottles being manufactured by several different companies. For example, the BAXTER (™) water bottle has a thread with a pitch of 0.104 inches, an annular ring around the neck below the thread and a seal at the bottom of the neck. The ABBOTT (™) water bottle has a thread having a pitch of 0.96 inches and a neck length of 0.844 inches. The MCGAW (™) water bottle has a neck length of 0.70 inches and a thread pitch of 0.88 inches. As such, a need developed so as to have a single cap which is adaptable to the varying thread configurations and neck lengths of the brands of water bottle.

Under certain circumstances, the water bottle is connected to the heater/probe unit of an endoscope. Under such circumstances, only water is drawn into the heater/probe unit. As water is being drawn into the heater/probe unit, air must enter the water bottle so as to allow pressures to equalize. Under existing practice, a hole is formed in the cap so as to allow air to freely enter the cap. Unfortunately, the air in the hospital environment can be contaminated with airborne bacteria and pathogens. Since the hospital air is being drawn into the water bottle, this air can contaminate the sterile water within the water bottle. As such, a need developed to develop an adapter cap wherein the airborne bacteria is prevented from entering the sterile liquid on the interior of the water bottle.

Under existing practice, the fitting which connects the water bottle to the air and water connections of the endoscope is formed so as to have a metal ring around the water connection. In existing practice, this metal ring is adhesively secured within a hole formed in the end of the fitting. Unfortunately, after repeated use, this metal fitting can become loosened. This is particularly the case when the metal fitting is secured by epoxy within the hole. The epoxy is subject to fracturing upon the exertion of torque and twisting forces. When the metal ring is loosened, the fitting is unsuitable for use with the air and water connections of the endoscope. As such, a need developed so as to assure a secure and permanent connection between the metal ring and the hole of the fitting.

It is an object of the present invention to provide a water bottle adapter for an endoscopic instrument which eliminates the need for the specialized water bottle.

It is another object of the present invention to provide such an adapter which can be used with conventional one liter water bottles existing in the hospital environment.

It is a further object of the present invention to provide such adapter which does not require the disposal or sterilizing of both the adapter and the water container.

It is a further object of the present invention to provide such an adapter which is easy to use, which significantly reduces costs, and is easy to manufacture.

It is a further object of the present invention to provide an adapter which allows for the water bottles to be properly connected to the new 140 series of endoscopes.

It is still another object of the present invention to provide an adapter which allows for the water container systems of existing endoscopes to be adapted and fitted to the new 140 series of endoscopes.

It is a further object of the present invention to provide an adapter which allows for connection to the water bottle which assures that the water transmitting tube has an end residing at the bottom of the water bottle.

It is still a further object of the present invention to provide an adapter which is transparent for easy viewing of the interior of the adapter.

It is a further object of the present invention to minimize costs associated with the sterilizing of existing water bottles.

It is another object of the present invention to provide a cap for the adapter which is suitable for attachment to the various brands of disposable water bottles.

It is still another object of the present invention to provide a cap for the adapter which establish a secure seal against the opening of the neck of the various water bottles.

It is a further object of the present invention to provide a cap for use with the adapter which prevents the introduction of airborne contaminants into the sterile environment of the water bottle.

It is still another object of the present invention to provide a fitting for the adapter which will prevent dislodgment of the metal ring and assure a long life for the fitting.

These and other objects and advantages of the present invention will become apparent from a reading of the attached specification and the appended claims.

SUMMARY OF THE INVENTION

The present invention is a water bottle adapter for use with an endoscopic instrument. The water bottle adapter of the present invention includes a cap having threads suitable for attachment to the threads on the neck of the water bottle, a first gasket member affixed to an interior surface of the cap, a second gasket member affixed to the first gasket member, an outer tube affixed to an opening in the cap, an inner tube extending through the outer tube and a fitting affixed to an end of the inner and outer tubes opposite the cap. The inner tube forms an air passing annulus on the interior of the outer tube. The inner tube extends outwardly of the end of the outer tube and through the opening in the cap. The fitting is adapted for attachment to the air and water connections of the endoscope.

In the present invention, the first gasket member is sandwiched between the second gasket member and the interior surface of the cap. The first gasket member is of a different material than the second gasket member. The first gasket member is more compressible and has a greater thickness than the second gasket member. The first gasket member is formed of a foam material. The second gasket member is formed of a rubber material. The first gasket member is adhesively fastened to the interior surface of the cap. The second gasket member is adhesively fastened to the first gasket member. A hole is formed in each of the gasket members so as to expose the opening in the cap and to allow the inner tube to extend through the hole and the gasket members.

In another embodiment of the present invention, the cap has an orifice formed therein. An air filter is affixed within the orifice. This air filter is a HEPA filter. The gasket members will have an elongated slot so as to allow the inner tube to pass therethrough and to allow the air filter to communicate with the interior of the cap.

In the present invention, the fitting has a first hole and a second hole formed at an end opposite the inner and outer tubes. The fitting has an annular member secured within the first hole. The annular member has a slot formed in a wall thereof. This slot engages a protrusion formed in the first hole. The annular member has an end which is flush with the end of the fitting opposite the inner and outer tubes. This slot is formed so as to open at an end of the annular member and through the wall of the annular member. The slot slidably receives the protrusion therein. The annular member is adhesively secured within the first hole.

BRIEF DESCRIPTION OF THE DRAWINGS

FIG. 8 is a cross-sectional view of the adapter body of the present invention as used with the fitting to the water bottle of the present invention.

FIG. 9 is an end view of the female connectors as used on the adapter body of the present invention.

FIG. 10 is an opposite end view of the adapter body of the present invention.

DETAILED DESCRIPTION OF THE INVENTION

Figure 1:
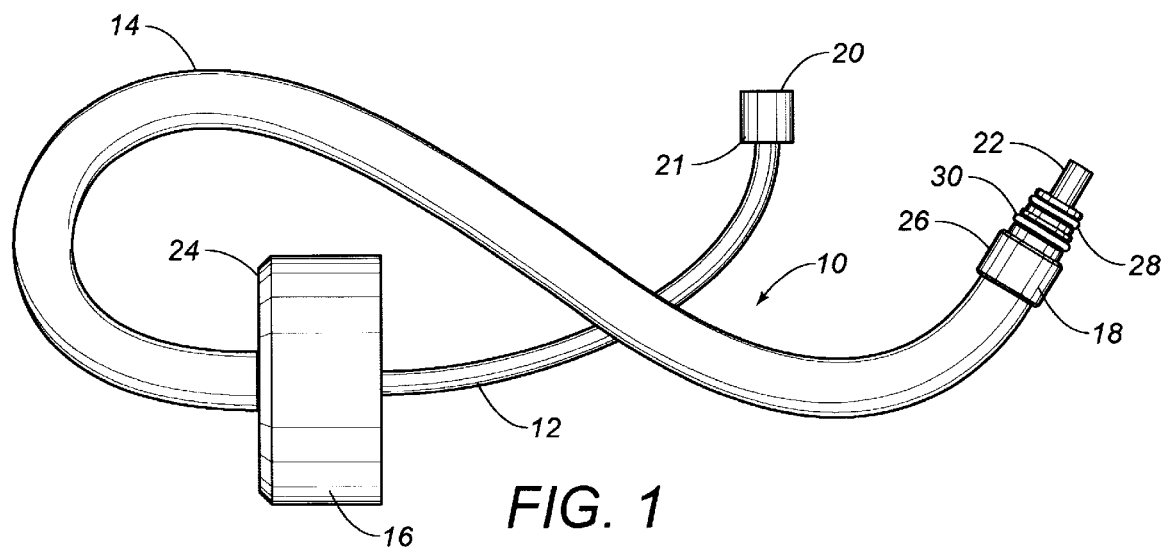
FIG. 1 is a side elevational view of the water bottle adapter in accordance with the preferred embodiment of the present invention.

Referring to FIG. 1, there is shown at 10 the water bottle adapter in accordance with an embodiment of the present invention. The water bottle adapter 10 includes an inner tube 12, an outer tube 14, a bottle cap 16, and a fitting 18. This fitting, as illustrated, is used for connecting to the air and water connections of an existing endoscope, but not to the new air and water connections of the 140 and 160 series of endoscopes. The inner tube 12 extends outwardly of the bottle cap 16 and has an opening at end 20. In normal use, the inner tube 12 will extend into the interior of the water bottle. The bottle cap 16 will be threadedly secured to the threaded neck of the water bottle. The inner tube 12 will extend through the cap 16, through the interior of the outer tube 14, and will terminate at the fitting 18. The inner tube 12 is made of a plastic or elastomeric material. A nozzle 22 is provided at the end of the fitting 18 so as to allow for the water from the inner tube 12 to be dispensed therefrom. The end 20 has a metallic anchor member 21 affixed thereto.

The outer tube 14 is also a flexible plastic or elastomeric tube. The outer tube 14 will extend from the back 24 of the bottle cap 16 and will terminate at the fitting 18. As will be described hereinafter, an annular passageway on the interior of the outer tube 14 is formed by the exterior of the inner tube 12 and the interior of the outer tube 14. This annulus will allow for the passage of air from the fitting 18 to the interior of the cap 16 as it is secured to a water bottle. As such, the necessary "pumping" effect can be achieved so as to allow for the passage of water into the end 20 of the inner tube 12. The outer tube 14 is secured to an outer tube fitting 26. A pair of O-rings 28 and 30 are provided on the exterior of the fitting 18 so as to allow the fitting 18 to be properly secured to the endoscopic instrument in the manner of conventional water bottle tubes.

In FIG. 1, it can be seen that the anchor member 21 is affixed to the end 20 of the inner tube 12. The anchor member 21 serves to assures that the end 20 of the inner tube 12 will reside adjacent to the bottom of the sterile water bottle. Conventionally, when the tubing 12 is formed, it will have a "memory" such that the tubing 12 will tend to recoil upwardly within the water bottle. As such, the end 20 of the inner tube cannot extend to the very bottom of the water bottle. As a result, not all of the water within the water bottle will be available for use. However, with the attachment of the anchor member 21 to the end 20 of the inner tube 12, a sufficient weight is achieved so as to overcome this "memory" of the inner tube 12. So as to avoid this connection, the anchor member 21 is ultraviolet glued to the ends 20 of the inner tube 12. Similarly, the fitting 18 will be ultraviolet affixed to the end of the outer tube 14 and to the inner tube therewithin. The cap 16 has inner threads which are particularly adapted for joining with the threads of the most popular available configurations of water bottles.

Figure 2:
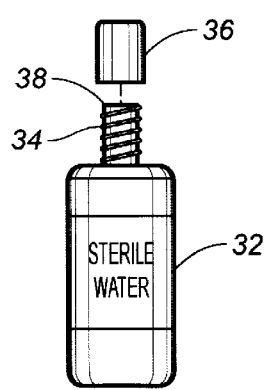
FIG. 2 is an exploded isolated view of an existing sterile water bottle.

FIG. 2 is an isolated view of a water bottle 32. The water bottle 32 is a one liter water bottle of a conventional type used in hospitals. The water bottle 32 is conventionally filled with sterile water. It is necessary to use sterile water since such water will pass to the interior of the human body during the process of cleaning the optic head of the endoscopic instrument. The water bottle 32 has an externally threaded neck 34. In normal use, a cap 36 is threadedly secured to the threaded neck 34 so as to prevent leakage or dispensing of the water from the interior of the bottle 32.

Figure 3:
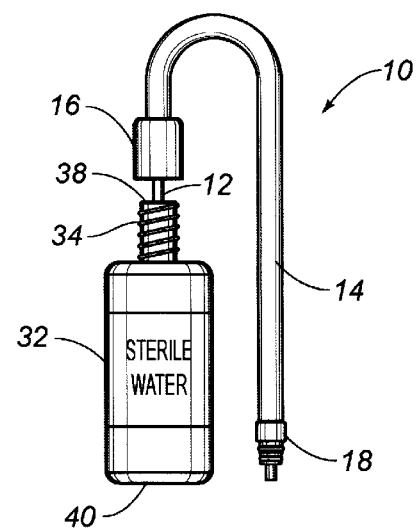
FIG. 3 shows the assembly of the water bottle adapter of the present invention with the existing hospital water bottle.

So as to effect the use of the adapter 10 of the present invention, it is necessary for the cap 36 to be threadedly removed from the exterior of the neck 34 of water bottle 32. The next step in the process of the present invention is shown in FIG. 3. As can be seen in FIG. 3, the inner tube 12 will be inserted into the opening 38 at the top of the neck 34 of the water bottle 32. Inner tube 12 will extend down into the interior of the water bottle 32 such that the end 20 of the inner tube 12 will reside adjacent to the bottom 40 of the water bottle 32. The use of anchor member 21 assures that the inner tube 12 will reside at the bottom 40 of the water bottle 32.

Once the inner tube 12 is inserted through the opening 34 of the water bottle 32, the bottle cap 16 will be moved downwardly to the opening 38 on the neck 34. The cap 36 can be rotated so as to threadedly secure the cap 16 around the exterior surface of the neck 34. Once the cap 36 is properly secured in its position, the adapter 10 is ready for attachment to the endoscopic instrument. The fitting end 18 is located at the opposite end of the outer tube 14 so as to allow for a quick connection to the endoscopic instrument. The interior of the cap has a special configuration, as will be described hereinafter in FIGS. 16–20.

Figure 4:
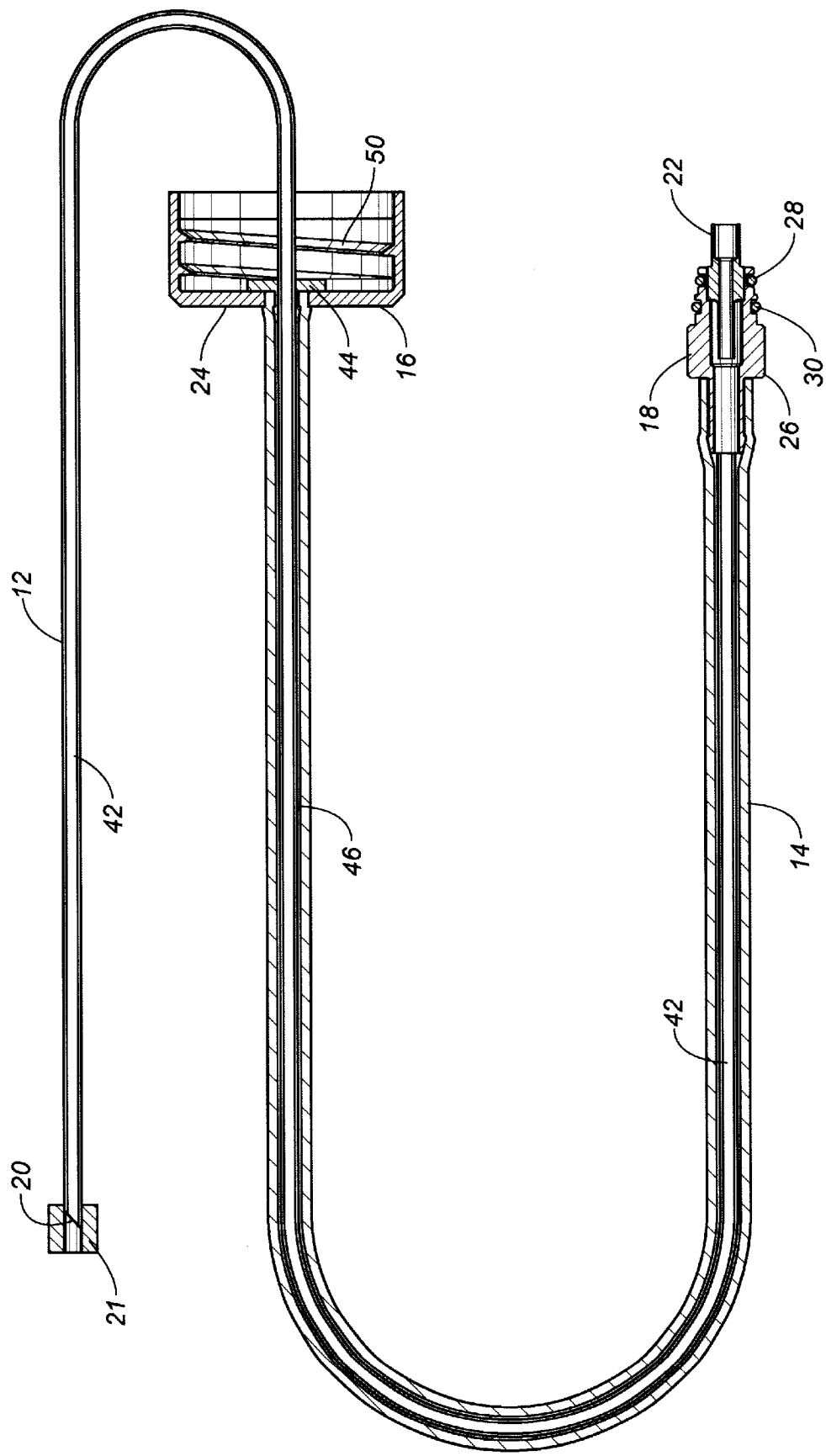
FIG. 4 is a cross-sectional view of the water bottle adapter in accordance with the preferred embodiment of the present invention.
Figure 5:
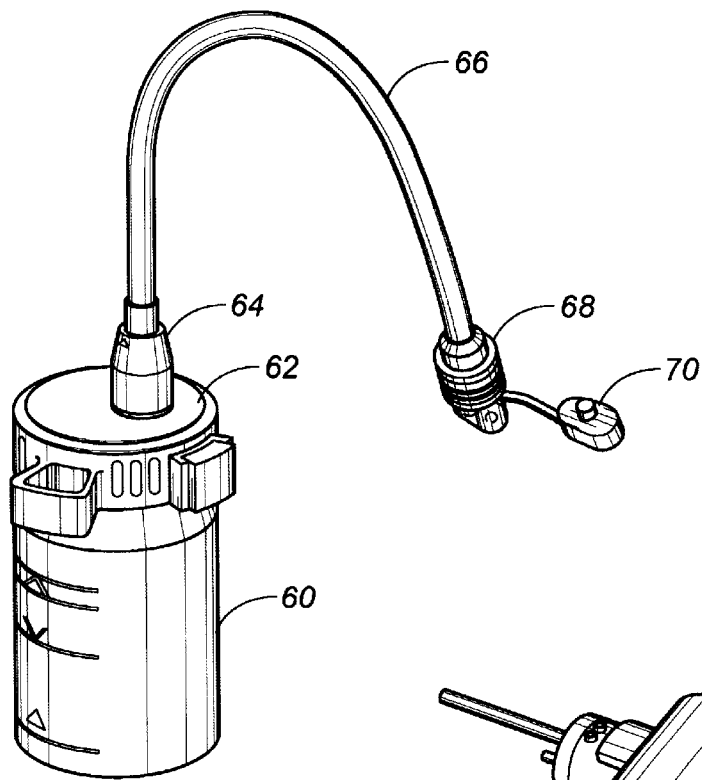
FIG. 5 is a perspective view of a prior art water container, and associated fittings, as used with the 140 series of endoscopes.
Figure 6:
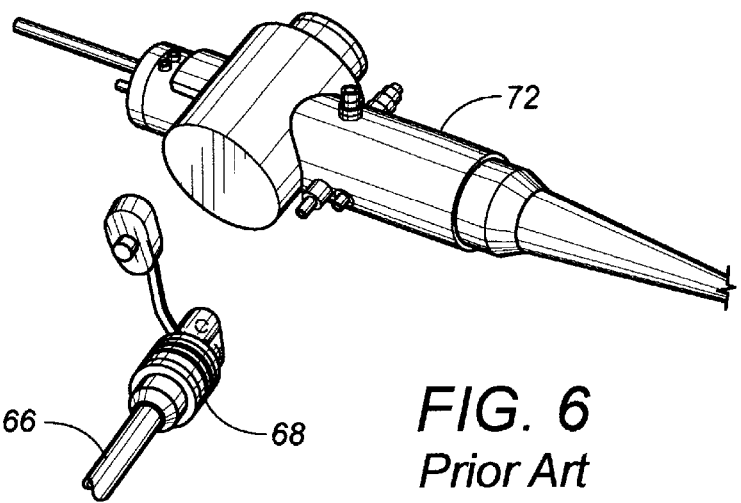
FIG. 6 is a perspective view showing the joining of the metal fitting of the water container of FIG. 5 with the 140 series of endoscopes.

FIG. 4 shows the interior arrangement of the inner tube 12, the outer tube 14, the cap 36 and the fitting 18. As can be seen, the inner tube 12 has an opening at end 20. Anchor member 21 is affixed to end 20. An interior passageway 42 extends through the length of the inner tube 12. This interior passageway, along with the inner tube 12, terminates at the inner tube fitting 22 at the distal end of the fitting 18.

The outer tube 14 has one end which is secured to the back 24 of the cap 36. A suitable fitting 44 allows the passage of the inner tube 12 through the interior of the outer tube 14. An annular passageway 46 is then formed between the inner surface of the outer tube 14 and the outer surface of the inner tube 12. The fitting 44 is positioned so as to allow air passing through this annular passageway 46 to enter the interior of the bottle onto which the cap 16 is secured.

The outer tube 14 is affixed to the outer tube fitting 26. Suitable O-ring seals 28 and 30 fit around the exterior of the fitting 18. In this manner, air is allowed to enter through the fitting 18 and through the annular passageway 46 between the inner tube 12 and the outer tube 14.

The cap 36 has interior threads 50 that are sized to fit on the various shapes and sizes of exterior threads on the neck 34 of the water bottle 32. It can be seen that the cap 36 shows the special configuration of the interior of the cap within a first gasket member 51 is affixed to an interior surface 53 of the cap 36. Similarly, a second gasket member 55 is affixed to a surface of the first gasket member 51 so as to sandwich the first gasket member 51 between the interior surface 53 and the second gasket member 55. The first gasket member 51 is of a different material than the second gasket member 55. The first gasket member 51 is of a more compressible material and is of a greater thickness that the second gasket member 55. Specifically, the first gasket member is formed of a foam material with adhesive on both sides. This foam gasket 51 gives greater flexibility and will facilitate the ability of the second gasket member 55 to establish a firm and tight seal with the end of the neck of the various size brands of water bottles. The foam gasket 51 gives proper spacing for the second gasket member 55 from the interior surface 53 of cap 36. The second gasket member 55 is of a FDA buna rubber material. The second gasket member 55 will be suitable for seating onto the top 38 of the water bottle.

The threads 50 have a special configuration also. The threads 50 are specially designed so as to match the variation in threads between the various brands of water bottle. Specifically, the threads 50 are buttress threads having a four milliliter pitch (the distance between the threads). As such, even though the thread designs of the various brands of water bottles are different, the particular pitch and shape of the threads 50 are configured so as to allow the cap 36 to be attached to the various types of water bottles.

In actual use, a controlled flow of air is maintained through the air passing annulus 46 so as to control the flow of water through the interior 42 of the inner tube 12. If more water flow is desired, then greater air pressure is delivered through the annular passageway 46 to the interior of the water bottle 32. If less water flow is desired, then less air pressure is applied.

FIG. 8 illustrates how the fitting 18 can be connected to the new 140 series of endoscopes. So as to allow the fitting 18 to be properly connected to the 140 series of endoscopes, it is necessary to employ adapter body 100. The adapter body 100 has a female air connector 102 and a female water connector 104 at end 106 of the adapter body 100. The female air connector 102 is sized and shaped so as to fit onto the male air connector 76 of the endoscope 72. Similarly, the female water connector 104 is sized and shaped so as to receive the male water connector 74 of endoscope 72. In actual use, an annular ring 105 is secured within the hole for the female water connector 104. The special configuration of this annular member 105 will be described hereinafter in connection with FIGS. 14 and 15. In general, the female connectors 102 and 104 are suitable for attaching to the male connectors of the 140 series of endoscopes.

An air passageway 108 will extend through the adapter body 100 so as to open, on the interior of the adapter body 100, and then so as to pass into the annular area between the outer tube and the inner tube of the water bottle system. Similarly, a water channel 110 is provided on the interior of the adapter body 100 so as to allow water to pass into the female water connector 104 from the interior of the adapter body 100 and from the interior 112 of the tube 114. As such, this allows water to be delivered to the endoscope from the water bottle. Suitable O-ring seals are incorporated throughout the adapter body 100 so as to achieve a strong liquid and airtight seal between the fitting 18 and the interior of the adapter body 100. Additionally, appropriate O-ring seals are provided on the female air connector 102 and the female water connector 104 so as to achieve a strong water and airtight fitting between the male and female connectors.

Figure 7:
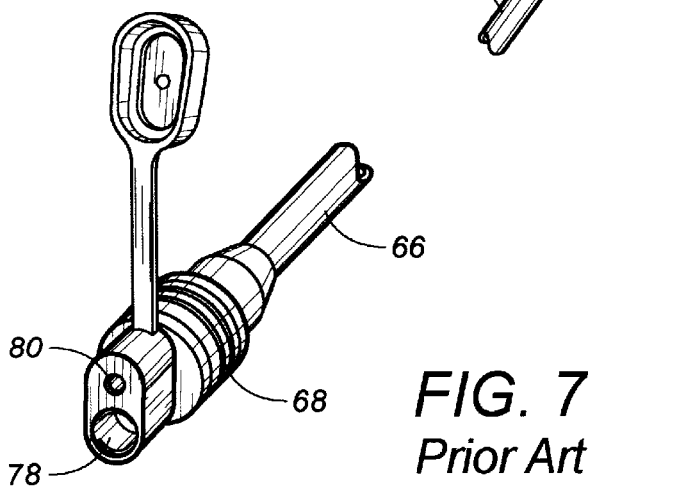
FIG. 7 is a perspective end view of the metal end fitting as used with the water container of FIG. 5.

FIG. 9 is a view of the end 106 of the adapter body 100. As can be seen, there is a small opening which illustrates the female air connector 102. A larger opening is provided below the female air connector 102 so as to illustrate the female water connector 104. As can be seen, the end 106 with its female air connector 102 and female water connector 104 has a similar configuration as the end view of the metal tip 68 as shown in FIG. 7. The annular member 105 is illustrated in FIG. 9 as extending around the hole of the female water connector 104. The annular member 105 is secured with an adhesive, such as epoxy, within the hole of the female water connector 104.

FIG. 10 is a view of end 116 of the adapter body 100. An opening 120 is provided so as to allow for the entry of the water passageway 122 of the fitting 18.

Figure 11:
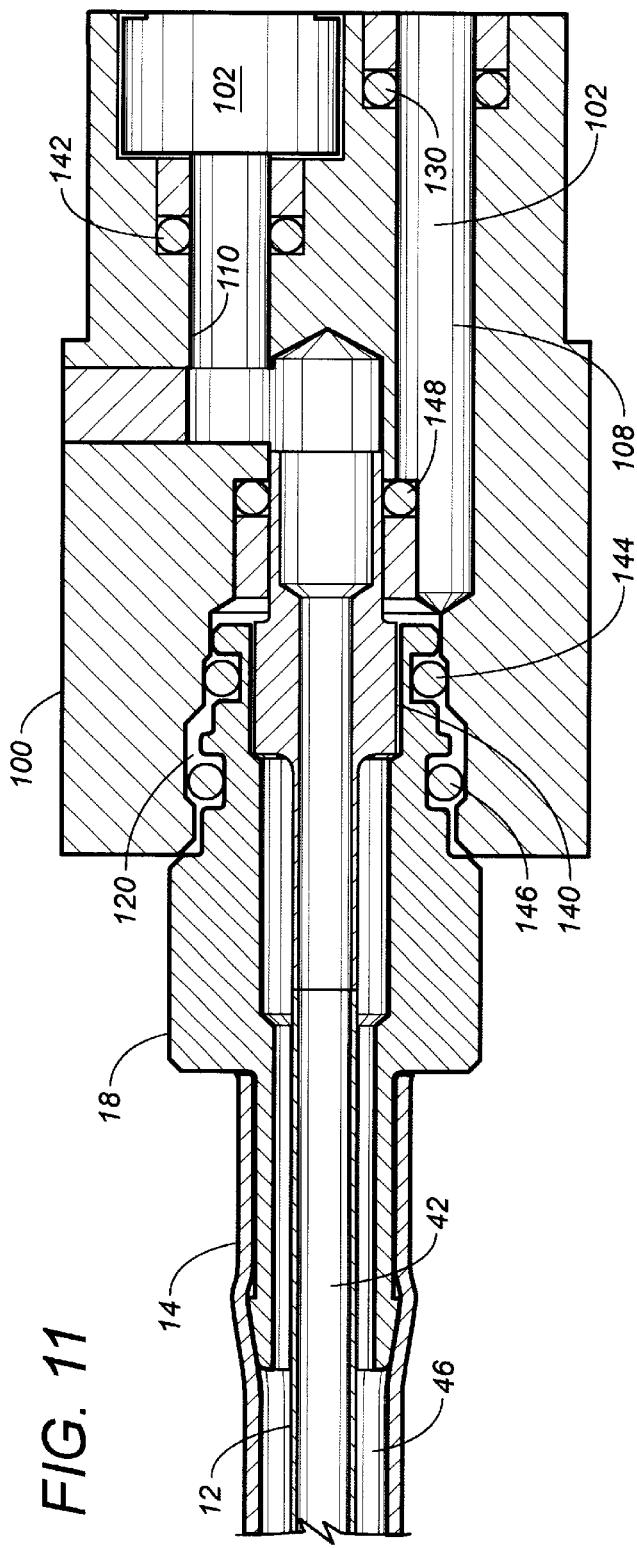
FIG. 11 is a cross-sectional view showing the joining of the adapter body with the fitting for the water bottle of the present invention.

FIG. 11 illustrates the manner in which the fitting 18 is connected onto the interior of the adapter body 100. Initially, it can be seen that the adapter body 100 has the female water connector 104 and the female air connector 102 at one end. The annular member 105 is illustrated as fastened within the hole of the female air connector 102 and extend so as to be flush with the end of the adapter body 100 opposite the fitting 18. An O-ring seal 130 is provided on the interior of the female air connector 102 so as to create a strong airtight seal with the exterior surface of the male air connector 76 of endoscope 72.

As was described herein previously, air will flow through the annular space 46 between the inner tube 12 and the outer tube 14. In the present invention, air can flow through the air passageway 108 through air channel 140 and into the annular space 46 between the inner tube 12 and the outer tube 14.

The female water connector 104 has a suitable size for receiving the exterior surface of the male water connector 74 of endoscope 72. A suitable O-ring seal 142 is provided on the water passageway 110 so as to create a water-tight seal between the exterior surface of the male water connector 74 and the inner surface of water passageway 110. Water will flow through water passageway 110 through the interior of the adapter body 100 so as to enter the water outlet 22. Water outlet 22 communicates with the interior 42 of the inner tube 12 so as to allow for the delivery of water from the water bottle to the endoscope instrument.

It can be seen that the fitting 18 is appropriately received within the opening 120 of the adapter body 100. O-ring seals 144 and 146 are provided on the exterior surface of the fitting 118 so as to create the necessary air and water-tight seal between the exterior surface of the fitting 18 and the interior surface of the opening 120. Another O-ring seal 148 is provided adjacent to the water outlet 22 so as to create a water-tight seal.

As can be seen in FIGS. 8–11, the present invention provides an adapter body 100 which allows for the receipt of a fitting 18 for the water bottle system of the present invention so as to allow it to be connected to the new 140 series of endoscopes. Additionally, the present invention provides an adapter body 100 which allows existing expensive water bottles which have been used for prior endoscope systems to also be used with the new 140 series of endoscopes. As a result, it is no longer necessary to purchase separate water bottles for the various endoscopes. Even though a hospital purchases the new 140 series of endoscopes, they can continue to use the existing equipment.

Since the cap 36 is adapted to standard one liter hospital water bottles, there is no need to purchase the specialized water bottle associated with existing water delivery systems for endoscopic instruments. After actual use, the adapter 10 can be disposed. Since there is no direct contact between the bodily fluids of the patient and the interior of the water bottle, the water bottle can be sterilized and reused or disposed of. The elimination of the specialized water container associated with existing water flow delivery systems for endoscopic instruments will greatly reduce the cost of such adapters.

Figure 12:
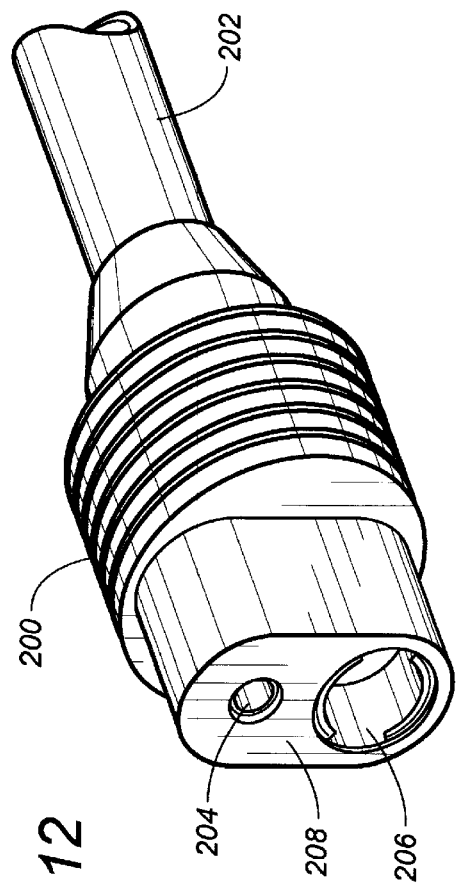
FIG. 12 is a perspective end view of the adapter body as permanently affixed to the end of the tubes.

FIG. 12 shows an alternative form of the embodiment shown in FIGS. 8–11. In FIG. 12, it can be seen that the adapter body 200 is permanently affixed to the tubing 202. As can be seen, the air connector female fitting 204 and the water connector female fitting 206 extend outwardly form the end 208 of the adapter body 200. In this embodiment of the present invention, the adapter body 200 is directly affixed to the end of tubing 202 without the use of the fitting 18. Alternatively, the adapter body 200 can be permanently affixed onto the fitting 18. In this embodiment of the present invention, the adapter body 200, along with the tubing 202, is formed of a transparent material. As such, visual observation can be used so as to detect any contaminants which may occur within the adapter body 200 or the tubing 202. Since the adapter body 200 is formed of a disposable polymeric material, the adapter body 200 and the tubing 202 can be disposed of after use. No sterilizing or autoclaving is required. A metallic annular member 207 is fitted and secured within the water connector female fitting 206. The specific design of this annular member 207 will be described hereinafter in FIGS. 14 and 15.

Figure 13:
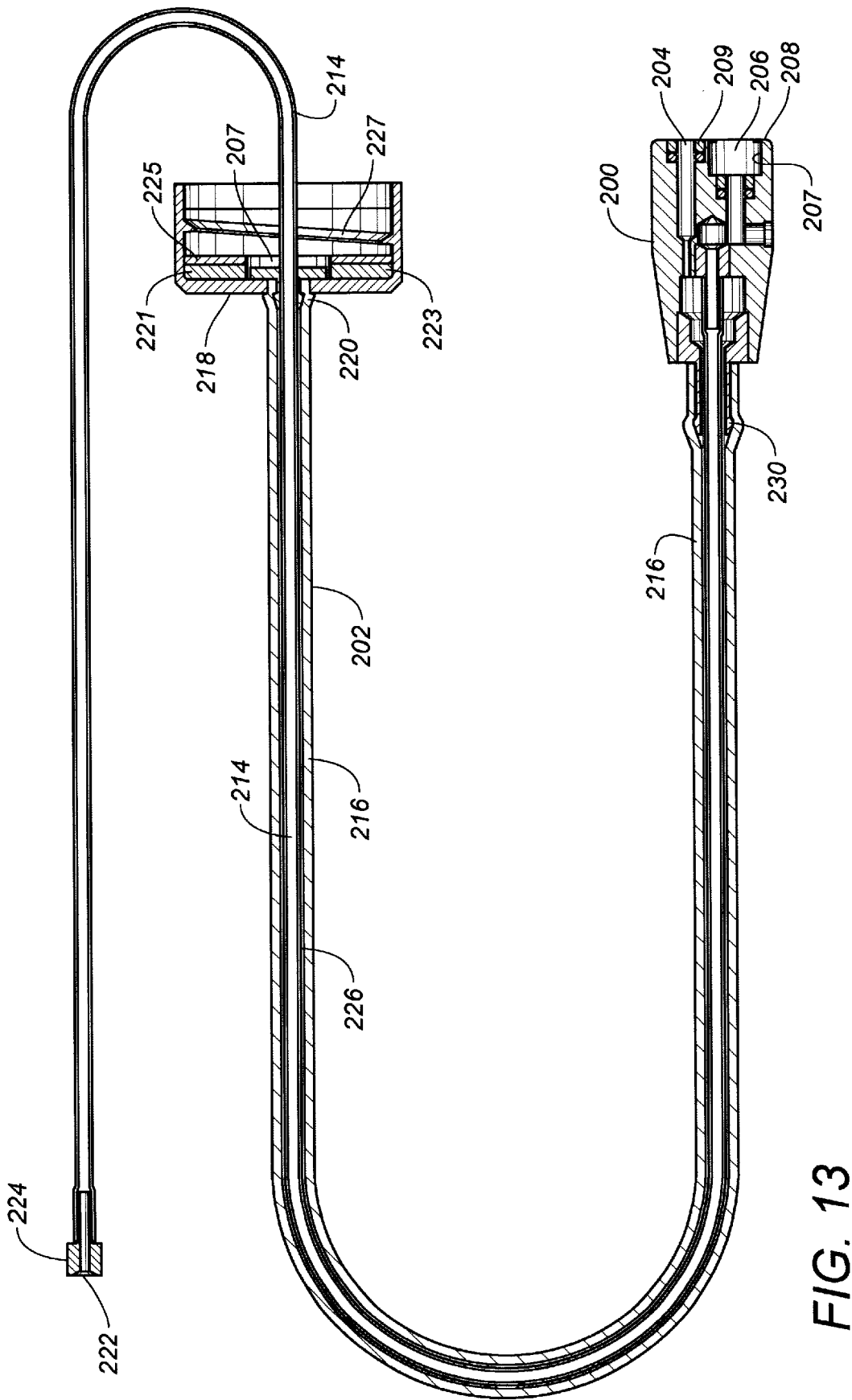
FIG. 13 is a cross-sectional view of the adapter as permanently affixed to the end of the tube.

FIG. 13 is a cross-sectional view of the complete apparatus in accordance with the teachings of FIG. 12. In FIG. 13, it can be seen that the adapter body 200 is connected to tubing 202. The tubing 202 has an inner tube 214 and an outer tube 216. The outer tube 216 is connected to the opening in the cap 218. Cap 218 is adapted for connection to existing one liter water bottles. The inner tube 214 will extend through the opening 220 in the cap 218 so as to extend to end 222. Ends 222 has a metallic anchor member 224 affixed thereto. The air passing annulus 226 is formed in the area between the inner tube 216 and the inner tube 214. In FIG. 13, it can be seen that the cap 218 has an interior surface 221. A first gasket member 223 is affixed against the surface 221. A second gasket member 225 is affixed against the surface of the first gasket member 223 opposite the interior surface 221. A hole 205 is formed in each of the gasket members 223 and 225 so as to allow the inner tube 214 to extend therethrough. The hole 205 also exposes the interior of the cap 218 to the air-passing annulus between the inner tube 214 and the outer tube 216. The cap 218 has a configuration of threads 227 similar to that described herein previously in connection with FIG. 4.

It can be seen that the adapter body 200 has female air passageway 204 and female water passageway 206 opening at end 208 of the adapter body 200. As can be seen, the female connector 204 has a channel which extends through the adapter body 200 so as to allow air to be emitted into the air-passing annulus 226. Similarly, the female water connector 206 is suitably connected to the interior of the inner tube 214 so as to allow water to pass therethrough. The outer tubing 216 is secured over a male connector 230 at the opposite end of the adapter body 200 from the end 208. The interior of the outer tube 226 can be ultraviolet sealed onto the male connector 230. As such, the adapter body 200 is non-removably affixed to the tubing 202. The female water passageway 206 has an annular member 207 secured therein. The annular member 207 is formed of a metallic material. An end of the annular member 207 will be flush with the end 209 of the adapter body 200.

Figure 14:
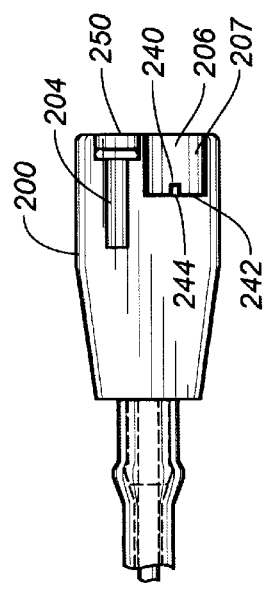
FIG. 14 is a side view of the fitting as used in the present invention.

FIG. 14 is a side view of the adapter body 200. Adapter body 200 is formed of a clear polymeric material so that the female connector 204 can be seen and the female water passageway 206 can be seen from the exterior. Importantly, the annular member 207 is illustrated as affixed within the female water passageway 206. The annular member 207 is a ring of metal material having a slot 240 formed at end 242. Slot 240 slidably receives a protrusion 244 formed in the polymeric material of the adapter body 200. An adhesive, such as epoxy, serves to maintain the annular member 207 in its desired position.

Figure 15:
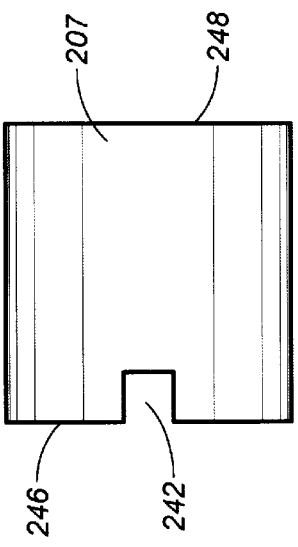
FIG. 15 is a detailed and enlarged side view of the annular member received within the hole of the fitting.

FIG. 15 is an illustration of the annular member 207 as separated from the adapter body 200. It can be seen that the slot 242 is formed at end 246 of the annular member 207. Slot 242 will open through the wall of the annular member 207 and also will engage the protrusion 244. When the slot 242 is positioned over the protrusion 244, the annular member 207 will be resistive of any twisting or turning movements caused by the installation of the adapter body 200 onto the air and water connections of the endoscope. Since epoxy is particularly fragile when torque is applied, the arrangement of the slot and protrusion will prevent destruction of the adhesive connection between the annular member 207 and the female water passageway 206. Annular member 207 is sized so that the end 248 will be flush with the end 250 of the adapter body 200.

Figure 16:
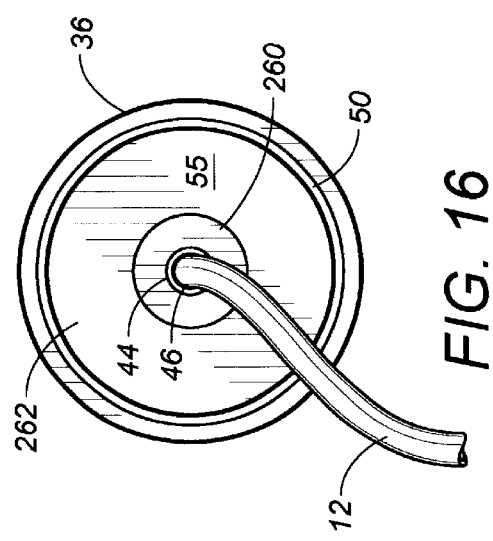
FIG. 16 is a bottom view of a preferred embodiment of the cap as used on the adapter of the present invention.

FIG. 16 shows an interior view of the cap 36 as originally shown in FIG. 4. Importantly, in this interior view, the cap 36 has threads 50 extending therearound. The inner tube 12 will extend outwardly of the fitting 44. A hole 260 is formed in the gasket members 53 and 55 so as to allow the inner tube 12 to pass therethrough and to allow the air passing annulus 46 to communicate with the interior area 262 of the cap 36. The surface of the second gasket member 55, as illustrated in FIG. 16, is flat so as to reside, in sealing relationship, upon the top of the neck of the water bottle.

Figure 17:
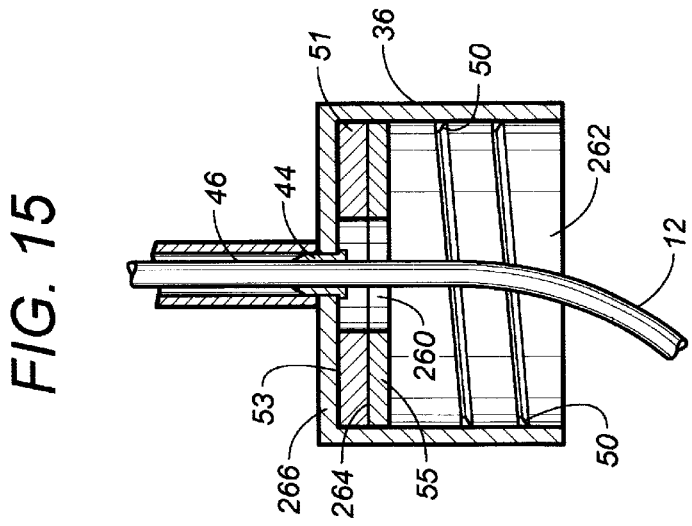
FIG. 17 is a cross-sectional view of the cap of FIG. 16.

FIG. 17 shows the arrangement of the cap 36 in cross-section. In particular, it can be seen that the first gasket member 51 is positioned so as to reside against the interior surface 53. Similarly, the second gasket member 55 is configured so as to be affixed, in adhesive relationship, against the surface 264 of the first gasket member 51. The first gasket member 51 is sandwiched between the interior surface 53 and the second gasket member 55. A hole 260 is formed in each of the gasket members 51 and 55 so as to allow the inner tube 12 to extend therethrough. A fitting 44 is secured to the top 266 of the cap 36 so as to allow the inner tube 12 to extend through the top 266 and to allow the air passing annulus 46 to open to the interior 262 of the cap 36. Threads 50 are buttress threads having a relatively wide spacing on the interior 262 of the cap 36.

Figure 18:
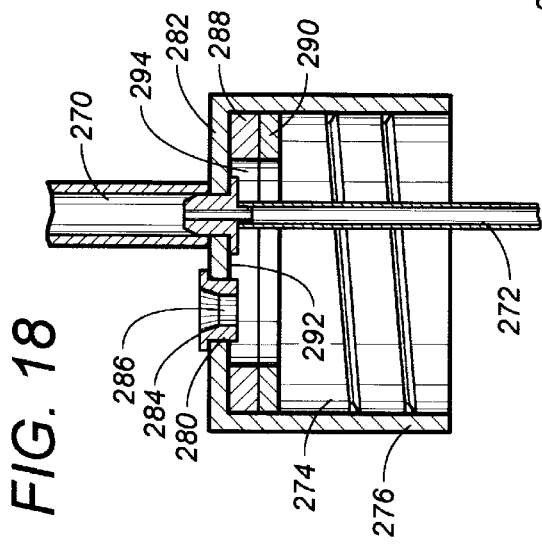
FIG. 18 is a cross-sectional view of an alternative embodiment of the cap as used with the adapter of the present invention.

FIG. 18 shows an alternative embodiment of the present invention. The alternative embodiment of FIG. 18 is used, in particular, with the heater/probe unit of an endoscope. The heater/probe unit of an endoscope will simply work by sucking on the water bottle. As such, water will enter a water tube 270 through tube 272 on the interior 274 of the cap 276. Similarly, air will enter through an orifice 280 formed through the top 282 of the cap 276.

In conventional practice, a small hole, such as orifice 280, would be formed in the cap 276 so as to allow air to enter the interior of the water bottle through the cap 276. Unfortunately, the passing of air through an open hole will allow contaminants to enter the sterile environment of the water bottle. In the present invention, a fitting 284 having a HEPA filter 286 is installed within the orifice. The HEPA filter will prevent the intrusion of airborne bacteria into the interior 274 of the cap 276.

In FIG. 18, it can be seen that the first gasket member 288 and the second gasket member 290 are affixed within the interior 274 of the cap 276 and against the interior surface 292. An elongated slot 294 is formed in each of the gasket members 288 and 290 so as to allow the tube 272 to extend therethrough and to allow the air filter 286 to be exposed to the interior 274 of the cap 276.

Figure 19:
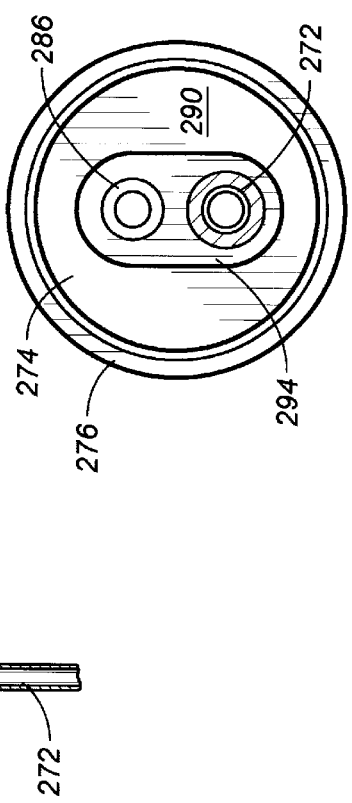
FIG. 19 is a cross-sectional view of a second alternative embodiment of the cap as used with the adapter of the present invention.

FIG. 19 shows a cap 300 suitable for use with PENTAX (™) endoscope systems. These PENTAX (™) endoscope systems use an air feed tube 302 and a water tube 304. An annulus 306 is formed between an outer tube 308 and the inner tube 304 so as to allow air from the interior 310 of the cap 300 (and the associated water bottle) to pass therethrough. In this PENTAX (™) endoscope system, air is pumped through the air tube 302, through the interior 310 of cap 300 and into the connected water bottle, so that the water will enter the water tube 304 and excess air will travel through the annulus 306.

In this embodiment, the first gasket member 312 is affixed against the interior surface 314 of the cap 300. As described before, the second gasket member 316 is affixed against the surface of the first gasket member 312 so as to sandwich the first gasket member 312 between the second gasket member 316 and the interior surface 304. An elongated slot 318 is formed in the gasket members 312 and 316 so as to allow air from the air tube 302 to be introduced into the interior 310 and to allow the inner water tube 304 to pass therethrough. Each of the gasket members 312 and 316 has a similar configuration to that described herein previously.

Figure 20:
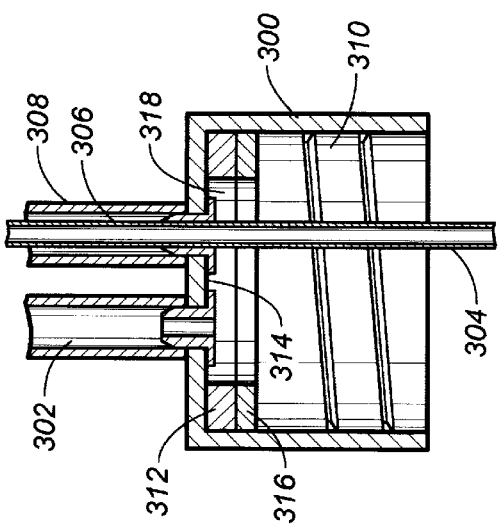
FIG. 20 is a bottom view showing the interior of the alternative embodiment of the cap as shown in FIG. 18.

FIG. 20 shows a bottom view of the alternative embodiment shown in FIG. 18. In particular, cap 276 has interior area 274. The second gasket member 290 has its elongated slot 294 suitably situated so as to expose the air filter 286 to the interior 274 and to allow the inner tube 272 to pass into the interior 274.

The foregoing disclosure and description of the invention is illustrative and explanatory thereof. Various changes in the details of the illustrated apparatus may be made within the scope of the appended claims without departing from the true spirit of the invention. The present invention should only be limited by the following claims and their legal equivalents.

I claim:

1. An adapter for a disposable water bottle for an endoscope comprising:

a cap having threads suitable for attachment to threads on the neck of the water bottle, said cap having an interior surface;

a first gasket member affixed to said interior surface of said cap;

a second gasket member affixed to said first gasket member such that said first gasket member is sandwiched between said second gasket member and said interior surface;

an outer tube affixed to an opening in said cap;

an inner tube extending through said outer tube, said inner tube forming an air passing annulus on an interior of said outer tube, said inner tube extending outwardly of an end of said outer tube and through said opening in said cap; and a fitting affixed to an end of said inner and outer tubes opposite said cap, said fitting adapted for attachment to air and water connections of the endoscope.

2. The adapter of claim 1, said first gasket member being of a different material than said second gasket member.

3. The adapter of claim 2, said first gasket member being more compressible and having a greater thickness than said second gasket member.

4. The adapter of claim 3, said gasket member being of a foam material, said second gasket member being of a rubber material.

5. The adapter of claim 1, said first gasket member being adhesively fastened to said interior surface, said gasket member being adhesively fastened to said first gasket member.

6. The adapter of claim 1, each of said first and second gasket members having a hole formed therein, said hole exposing said opening in said cap, said inner tube extending through said hole of said first and second gasket members.

7. The adapter of claim 1, said cap having a second opening formed therein, said second opening having a tube connected thereto, said first and second gasket members having an elongated slot formed therein so as to expose said second opening and to allow said inner tube to pass through said elongated slot.

8. The adapter of claim 1, said cap having an orifice formed through said cap so as to open adjacent said interior surface, the adapter further comprising:

an air filter affixed within said orifice.

9. The adapter of claim 8, said air filter being a HEPA filter.

10. An adapter for a disposable water bottle for an endoscope comprising:

a cap having threads suitable for attachment for threads on the neck of the water bottle;

an outer tube affixed to an opening in said cap;

an inner tube extending through said outer tube, said inner tube forming an air passing annulus on an interior of said outer tube, said inner tube extending outwardly of an end of said outer tube and through said opening in said cap;

a fitting affixed to an end of said inner and outer tubes opposite said cap, said fitting adapted for attachment to air and water connections of the endoscope; and an air filter affixed within another opening in said cap.

11. The adapter of claim 10, said air filter being a HEPA filter.

12. The adapter of claim 10, further comprising:

a gasket affixed to an interior surface of said cap, said gasket having a hole formed therein so as to allow said inner tube to pass therethrough and to allow said air filter to communicate with an interior of said cap.

13. The adapter of claim 12, said gasket comprising:

a first gasket member affixed to said interior surface of said cap; and a second gasket member affixed to said first gasket member such that said first gasket member is sandwiched between said second gasket member and said interior surface.

14. The adapter of claim 13, said first gasket member being more compressible and having a greater thickness than said second gasket member, said first gasket member being of a foam material, said second gasket member being of a rubber material.

15. An adapter for a disposable water bottle for an endoscope comprising:

a cap having threads suitable for attachment to threads on the neck of the water bottle;

an outer tube affixed to an opening in said cap;

an inner tube extending through said outer tube, said inner tube forming an air passing annulus on an interior of said outer tube, said inner tube extending outwardly of an end of said outer tube and through said opening in said cap; and a fitting affixed to an end of said inner and outer tubes opposite said cap, said fitting adapted for attachment to air and water connections of the endoscope, said fitting having a hole formed at an end opposite said inner and outer tubes, said fitting having an annular member secured within said hole, said annular member having a slot formed in a wall thereof, said slot engaging a protrusion formed in said hole.

16. The adapter of claim 15, said annular member having an end flush with said end of said fitting opposite said inner and outer tubes.

17. The adapter of claim 15, said slot formed so as to open at an end of said annular member and through a wall of said annular member, said slot being slidably received by said protrusion.

18. The adapter of claim 15, said annular member being adhesively secured in said hole.

19. The adapter of claim 15, said fitting and said protrusion being integrally formed of a polymeric material, said annular member being of a metallic material.

20. The adapter of claim 15, further comprising:

a gasket affixed to an interior surface of said cap, said gasket having a hole formed therein so as to allow said inner tube to pass therethrough, said gasket comprising:

a first gasket member affixed to said interior surface of said cap; and a second gasket member affixed to said first gasket member such that said first gasket member is sandwiched between said second gasket member and said interior surface.

\* \* \* \* \*